US006569682B2

(12) United States Patent
Elliott et al.

(10) Patent No.: US 6,569,682 B2
(45) Date of Patent: May 27, 2003

(54) HEMATOLOGY CONTROL PRODUCT WITH INCREASED CLOSED VIAL STABILITY

(75) Inventors: Michael Elliott, Fort Lauderdale, FL (US); Dana B. Jacobs, Cooper City, FL (US); Nery Ortiz, Miami, FL (US); Wayne Goldson, Sunrise, FL (US); Penny Whitley, Lawrenceville, GA (US); Theodore J. Gerula, Fort Lauderdale, FL (US)

(73) Assignee: Coulter International Corp., Miami, FL (US)

( * ) Notice: Subject to any disclaimer, the term of this patent is extended or adjusted under 35 U.S.C. 154(b) by 0 days.

(21) Appl. No.: 09/917,452

(22) Filed: Jul. 27, 2001

(65) Prior Publication Data

US 2003/0044988 A1 Mar. 6, 2003

(51) Int. Cl.[7] ................................................. G01N 31/00
(52) U.S. Cl. .............................. 436/10; 436/8; 436/16; 436/18; 436/63; 252/408.1; 435/2
(58) Field of Search ................................ 436/8, 10, 16, 436/18, 63; 252/408.1; 435/2, 4, 29

(56) References Cited

U.S. PATENT DOCUMENTS

| 3,558,522 | A | * | 1/1971 | Louderback et al. .......... 436/10 |
| 3,873,467 | A | | 3/1975 | Hunt |
| 4,290,774 | A | | 9/1981 | Girgis et al. |
| 4,358,394 | A | | 11/1982 | Crews et al. |
| 4,489,162 | A | * | 12/1984 | Hawkins et al. ............. 424/532 |
| 4,579,824 | A | * | 4/1986 | Louderback et al. ...... 252/408.1 |
| 4,698,312 | A | | 10/1987 | Wong et al. |
| 4,704,364 | A | | 11/1987 | Carver et al. |
| 4,777,139 | A | | 10/1988 | Wong et al. |
| 5,320,964 | A | * | 6/1994 | Young et al. .................. 436/10 |
| 5,380,664 | A | * | 1/1995 | Carver et al. .................... 435/2 |
| 5,512,485 | A | * | 4/1996 | Young et al. .................. 436/10 |
| 5,529,933 | A | | 6/1996 | Young et al. |
| 5,532,139 | A | * | 7/1996 | Miller ........................ 324/71.1 |
| 5,994,139 | A | * | 11/1999 | Jacobs et al. ............. 252/408.1 |
| 6,362,003 | B1 | * | 3/2002 | Young et al. ................ 424/532 |

OTHER PUBLICATIONS

Stadler et al. Influence of Cold Storage Altered Red Blood Surface on the Function of Platelets. Journal of Medicine, vol. 25, No. 6, 1994, pp. 353–361.*

* cited by examiner

Primary Examiner—Maureen M. Wallenhorst
(74) Attorney, Agent, or Firm—Howson & Howson; Mitchell E. Alter (57) ABSTRACT

An improved blood suspension media for hematological compositions, having particular utility with a red blood cell component for devices using electronic and optical means for blood determinations, and processes for using the suspension media. The suspension media finds particular utility in providing the hematology control product with a stable and consistent MCV and RDW for an extended product shelf life.

22 Claims, 3 Drawing Sheets

HEMATOLOGY CONTROL PRODUCT WITH INCREASED CLOSED VIAL STABILITY

FIELD OF INVENTION

This invention relates to a novel suspension media for hematological compositions, having particular utility with a red blood cell component, for devices using electronic and optical means for blood determinations, and processes for using the suspension media.

BACKGROUND OF THE INVENTION

It is evident that a hematology control product must accurately indicate, on a comparative basis, what a test sample of fresh blood constitutes with regard to the determinations in question. It is further evident how important it is for the control product to simulate fresh blood, since blood components, such as red blood cells, can hemolyze slowly and undergo changes in size and shape within hours after removal from a blood donor. Similarly, white blood cells suffer degenerative changes.

Suspending medium formulations are designed for the purpose of stabilizing the attributes of the cells and/or particles suspended in them, and to have antimicrobial properties sufficient to inhibit the growth of possible contaminating microorganisms. The specific parameters of the red and white blood cells that are desirable to be measured dictate some of the necessary characteristics of a suitable suspension media for a hematology control product. It is desirable to know the volume of the red cell. Once this measurement is ascertained and the red cells have been counted, the packed cell volume or hematocrit can be computed. Therefore, the suspension media of the control product should be capable of equilibrating and stabilizing the volume of red blood cells in the sample so that its mean corpuscular volume (MCV) and red blood cell distribution width (RDW) can be measured.

Because of the sensitivity of the components of a hematology control product, such as the red blood cell component, white blood cell component, and platelet component, to the chemical compounds contained in a suspension media, it has been difficult to find a combination of chemical compounds that do not degrade or undesirably alter the characteristics of the blood cell components to be analyzed, especially over varied storage times. Frequently, a chemical compound is added to maintain the stability of a blood cell component or a certain functional property, but which might detrimentally affect one or more physical parameters of the blood cells or other blood cell determinations.

One disadvantage of prior art suspension media of hematology control products is that when used in conjunction with a red blood cell component, the control product has a short closed vial storage life. After the control product storage life, the control product does not simulate one or more of the specific parameters of the blood cells that are desirable to be measured.

Historically the effectiveness of an individual suspending media formulation has been measured by the amount of stabilization (amount of change) observed for those specific attributes of cells and/or particles that are known to change or exhibit defined trends. It is well known that mammalian red blood cells (RBC's) used in the formulation of "whole blood" hematology controls exhibit changes in their MCV and RDW over time. It is important for the red blood cell component in the hematology control product to maintain an MCV within a defined range over a sufficient period of time in order to adequately assist in the calibration, operation, and accumulation of quality assurance data for a multi-parameter automated hematology instrument. Typically, manufacture specifications provide for a deviation of less than 6 femtoliter, and preferably less than 4 femtoliter, change from the highest MCV value to the lowest MCV value during the product's useful life. Changes greater than 6 femtoliter do not provide the necessary utility for the hematology control product. Concomitantly, the RDW should remain consistent over a sufficient period of time to provide the necessary utility for the hematology control product.

One general approach has been used to confer some degree of stability, that is to reduce the amount of MCV change, exhibited by the RBC's utilized in "whole blood" control. This general approach was shown by Hunt U.S. Pat. No. 3,873,467 (1975) and Wong et al U.S. Pat. No. 4,777,139 (1988) and U.S. Pat. No. 4,698,312 (1987), who used small amount of various aqueous aldehydes to stabilize the shape and size of suspended RBC's. However, one of the disadvantages of the stabilized RBC preparations described by Wong et al—U.S. Pat. No. 4,777,139 (1988) is that the stabilization period required before the exhibited MCV changes become minimal is dependent on the initial level or size of the treated preparation. Equilibrations took approximately 35, 25, and 10 days for Levels I, II, and III respectively. Once, however the MCV valued stopped changing, they remained constant (within tolerances of 1 MCV unit) for 90 days or longer. However, these unequal equilibration times increase the logistical difficulty in implementing these teachings in a manufacturing setting.

Another disadvantage of the prior art media is that, when used in conjunction with red blood cells and fixed human white blood cells or white blood cell analogs that have been stored in a closed vial for an extended period of time, the control product does not accurately indicate, on a comparative basis, what a test sample of fresh blood constitutes with regard to the determinations in question.

Not withstanding the prior art suspension media, there still exists a need for new suspension media for use in a hematology control product such that a stored closed vial of the hematology control product indicates upon analysis, on a comparative basis, what a test sample of fresh blood constitutes with regard to the determinations of MCV and RDW. The increased shelf life avoids the problems associated with manufacturing logistics and customer dissatisfaction of obtaining products with a shortened time in which the products can be used.

SUMMARY OF THE INVENTION

The present invention relates to a hematology control product comprising a closed vial of a lyseable red blood cell component and a xanthine compound in an isotonic suspension medium. The xanthine compound is in an amount sufficient to provide extended shelf life of the hematology control product and the lyseable red blood cell component is present in an amount sufficient to be measurable with an automated hematology instrument. The hematology control product has a reported MCV which corresponds substantially with the MCV of human whole blood. The hematology control product has an osmolality from about 200 to 400 milliosmoles. Preferably, the xanthine compound is present in an amount from about 0.1 to 1.0% by weight/volume. More preferably, the xanthine compound comprises caffeine.

The hematology control product can further contain compatible preservative compositions in an amount sufficient to provide fungicidal and bactericidal activity. In addition, the hematology control product can contain one or more pH adjusting agents to provide a pH in the range from approximately 5.8 to 6.8.

In a further embodiment, the hematology control product further contains a white blood cell component. Preferably, the white blood cell component simulates at least three subpopulations of white blood cells.

In still a further embodiment, the hematology control product contains a white blood cell component which simulates at least four subpopulations of leukocytes.

The present invention also relates to a method of using the above described hematology control product to determine the accuracy and reproducibility of the operation of a hematology instrument comprising the steps of:
  a) providing the hematology control product comprising a lyseable red blood cell component and a xanthine compound in an isotonic suspension medium, wherein the xanthine compound is in an amount sufficient to provide extended shelf life of the hematology control product and wherein the lyseable red blood cell component is present in an amount sufficient to be measurable with an automated hematology instrument and wherein the hematology control product has an reported MCV which corresponds substantially with the MCV of human whole blood, and wherein the hematology control product has a known reference value for each component type present in the product;
  b) determining the reference value for each component type in the hematology control product with an automated hematology instrument; and
  c) comparing the reference value for each component type obtained from step b) above with the known reference value for each component type from step a) above.

In a preferred embodiment, the method uses a mean cell volume value of the blood cell as the reference value. In addition, or in the alternative, the method can use a red blood cell distribution width value of the blood cell as the reference value.

DETAILED DESCRIPTION OF THE INVENTION

The present invention provides an improved isotonic blood suspension media. The suspension media is especially suitable for hematology control products that are analyzed by electronic and optical measurements resulting in analysis, enumeration and differentiation of blood cells and blood cell components. The suspension media finds particular utility to preserve the shelf life of a hematology control product over a longer period of time. A longer shelf life provides the manufacturer of the hematology control product with distribution channels for the product not previously available in shorter life products. In addition, the longer shelf life provides benefits to the end user by enabling the end user to purchase quantities of hematology products for subsequent use rather than purchasing a new supply of control products only after the existing supply has been exhausted or expired due to a shorter shelf life.

In a first embodiment, the suspension media is useful as a suspending media for components contained in a hematology control product used in the determination of red blood cell measurements. Measurements of the hematology control product can include cell size, shape, content and volume. Measurements can be made using light scatter, low frequency current, radio frequency current, fluorescence and combinations thereof. In a second embodiment, the suspension media is useful as a suspending media for additional components contained in the hematology control product used for the further differentiation of white blood cells into three subpopulations. In a third embodiment, the suspension media is useful as a suspending media for additional components contained in the hematology control product used for the further differentiation of white blood cells into at least four subpopulations of leukocytes. The suspension media finds particular utility in preserving the MCV and RDW of the red blood cell component of a hematology reference control for the extended shelf life.

The suspension media should have characteristics to make it compatible with its intended use. First, the compositions in the suspension media should not degrade the components in the hematology control composition during the shelf life of the hematology control product. The shelf life of the hematology control product takes into account the time from manufacture of the product through the time of customer usage of the product. Preferably, the suspension media causes the hematology control product to have a shelf life greater than 60 days, preferably greater than 75 days and most preferably greater than 90 days. It has been found that the combination of compositions in the present formulation meets this requirement.

The suspension media contains a first composition comprising an aqueous solution of a xanthine compound, which acts as a metabolic modifier of the red blood cells in an amount sufficient to provide extend shelf life of a hematology control product that contains red blood cells. Examples of the xanthine compounds include caffeine and pentoxifylline ($C_{13}H_{18}N_4O_3$ sold by Sigma Chemical Company, St. Louis, Mo.). The first composition is used in an amount effective to provide a hematology control product containing red blood cells with a stable red blood cell MCV over an extended period of time. The preferred amount of the first composition is from about 0.1 to 1.0% by weight/volume, and more preferably from about 0.2 to 0.7% w/v. It has been found that xanthine compounds in excess of the 1.0% w/v do not provide additional shelf life stability and have a tendency at higher concentrations to degrade the open vial stability of the hematology control product.

The suspension media also contains one or more suitable pH adjusting agents to provide a pH in the range from approximately 5.8 to 6.8, preferably from approximately 6.0 to 6.5. At pH levels higher or lower than the stated pH range, the MCV of the red blood cell component is found to deteriorate such that the MCV measurement of the control product is not optimally useable as an indication of the proper functioning of the instrument for this measurement. Examples of pH adjusting compositions which are suitable to impart the required pH include acids, typically citric, hydrochloric or sulfuric, and bases, such as alkali metal hydroxides and such other agents as known to those skilled in the art. Other acids may be substituted provided that they do not interfere with the analysis of the blood sample. Examples of acceptable pH adjusting agents include trisodium citrate and sodium phosphate. Examples of acceptable alkali metal hydroxides include sodium hydroxide and potassium hydroxide.

The suspension media also contains one or more suitable osmolality agents which provide an osmolality in a range effective to maintain the red blood cells from lysis. The alkaline metal chloride and alkaline metal sulfate can used to provide a suitable osmolality so as not to adversely affect the blood component in the hematology control product. Generally, the suspension media will be iso-osmotic. More specifically, the osmolality will be about 200 to 400 milliosmoles (mOsm), and preferably from 250 to 350 mOsm and most preferably from 280 to 330 mOsm. Control of the osmolality concomitantly affects the red blood cell MCV. Suitable osmolality and tonicity adjusting agents include sodium chloride, potassium chloride, lactose, dextran and such other compounds as known to those skilled in the art.

Ion balance is one of several factors that effect water flux across the cell membrane. It is believed that each of the major ions present in the suspension media should be present in an amount from approximately 0.001 to 0.100 moles. The major ions include potassium, sodium, chloride, phosphate and sulfate. The ions can be obtained from the adjusting agents and osmolality agents. At this time, it is unknown whether the functioning of these ions contributes to the extended shelf stability.

The suspension media for the hematological control product can include optional compatible preservative compositions that provide fungicidal and bactericidal activity, and optional supplementary compositions such as dextran, ammonium chloride and dihydroxyacetone, dioctyphthalate, adenosine monophosphate and inosine.

The preservative composition avoids fungal or bacterial growth which might adversely affect the physical characteristics or functionality of the suspension media. Preferably, the suspension media will not contain sodium 2-pyridinethiol-1-oxide (sodium omadine) or sodium fluoride. It has been found that the sodium omadine is unstable to light and oxidizing agents which can adversely affect product functionality. The use of sodium fluoride is not a suitable preservative since it has been found to react with glass cuvettes.

Suitable preservative compositions include sodium penicillian G, dihydrostreptomycin sulfate, 5-fluorouracil, imidazole, kanamycin sulfate, gentamycin sulfate and neomycin sulfate. However, the neomycin sulfate may affect the MCV of the red blood cells. The quantity of the preservative composition should not adversely affect the analysis of the hematology control product. The quantity of the preservative component can be determined by routine experimentation by one skilled in the art, and is typically less than 0.5% by weight of the suspension media.

A suspension media composition according to this invention is illustrated in Table 1, below:

TABLE 1

SUSPENSION COMPOSITION

| Component | Range (grams/liter) | Preferred (grams/liter) |
| --- | --- | --- |
| xanthine compound | 1–10 | 2–7 |
| adenosine monophosphate | 0.1–1.0 | 0.2–0.8 |
| inosine | 0.1–1.0 | 0.2–0.8 |
| pH adjusting agents sufficient to obtain | pH 5.8–6.8 | pH 6.0–6.5 |
| osmolality adjusters sufficient to obtain | 200–400 mOsm | 250–350 |
| preservative | effective amount | 2.0–6.0 |
| water | fill to 1 liter | |

The suspension media is used with a component comprising one or more blood cells (i.e. cells handled or treated to simulate such a component as found in whole blood) or their analogs (collectively referred to as blood cell components), that may or may not be fixed, stabilized, or prepared by other treatment prior to final suspension in the suspending media to form a hematology control product. The hematology control product can be used in multi-parameter automated hematology instruments. When measured by the instrument, the hematology control composition would assist in the calibration, operation, and accumulation of quality assurance data for the multi-parameter automated hematology instrument.

It will be appreciated that the term "hematology control composition" as used herein means one or more blood components (i.e., blood constituents as well as analogs thereof, which when combined or used alone, sufficiently simulate the relevant characteristics of whole blood for which the instrument tests. The hematology control composition comprises stabilized red blood cells which provides a red blood cell parameters, such as count, MCV and RDW. In addition, the hematology control composition contemplates the addition of a white blood cell component which simulates at least three, and preferably five subpopulations of white blood cells. The hematology control composition further contemplates the addition of other blood components to resemble corresponding components in whole blood such as reticulocytes, platelets and nucleated red blood cells.

In different embodiments, the blood cell components may be derived from a source that will exhibit the size, shape or other measurable characteristics of human, animal, or other whole blood. By way of non limiting examples, U.S. Pat. Nos. 3,873,467; 4,198,206; 4,219,440; 4,264,470; 4,299, 726; 4,358,394; 4,436,821; 4,390,632; 4,704,364; 4,777, 139; 5,008,021; 5,262,327; 5,270,208; 5,320,964; 5,380, 664; 5,432,089; 5,460,797; 5,512,485; 5,672,474; 5,677, 145; 5,731,205; 5,811,099; 5,981,282; 6,200,500; and 6,221, 668, which are each hereby incorporated by reference, each contain examples of these types of blood cell components.

In a first embodiment, the suspension media is useful as a suspending media for the red blood cell component contained in a hematology control product which are used in the determination of red blood cell measurements. Preferably, the red blood cell component comprises red blood cells of human origin. In addition, it is believed that analog blood cells from any suitable animal may be employed. However, if the red blood cells are fixed or stabilized with an aldehyde fixative, it is presently believed that the beneficial effects of the suspension media to provide long term shelf stability is minimized since the red blood cells have a marked decrease in metabolically activity.

The following examples illustrate the method of using the suspension media of this invention. All product samples were tested on a COULTER COUNTER® STKS™ hematology analyzer (Beckman Coulter, Inc., Miami, Fla.).

EXAMPLE 1

Hematology Control Product with a Red Blood Cell Component

In the present embodiment, the component of the control that is used to simulate the characteristics of red blood cells in whole blood is prepared from a bio-compatible material. More specifically, the material is a cellular biological material, and preferably the material is human red blood cells. The cells as provided are separated from the liquid medium or supernatant in which it is supplied through any suitable separation technique, including but not limited to centrifugation, filtration, or the like. The cells are washed in a series of one or more (e.g., 3) consecutive washing steps, pursuant to which excess supernatant is removed. The cells preferably are washed in a phosphate buffered solution. After washing, the cells are suspended in the suspension media of Table 1 at a desired concentration of red blood cells per volume. The cells have a stabilized MCV and RDW after approximately 25 days of being combined with the suspension media regardless of the red cell concentration. More specifically, the equilibration time of suspending the cells in the suspension media enables the cells to obtain a stable MCV and RDW. During the equilibration period, the MCV and RDW change rapidly until each reaches a stable rate of change which enables it to be used as a hematology control product.

The xanthine compound consists of caffeine at a concentration of 5 gram/liter. Different concentrations of red blood cells provide a hematology control product for normal and abnormal levels. For example, for a normal hematology control product the concentration of red blood cells is approximately 4,000,000 red blood cells per microliter ($\mu l$) which is referred to as containing a normal level of red blood cells; for an abnormal hematology control product the concentration of red blood cells is approximately 1,800,000 RBC/$\mu l$ which is referred to as a containing a low level of red blood cells; and for another abnormal hematology control product the concentration of RBC is approximately 5,400,000 RBC/$\mu l$ which is referred to as containing a high level of red blood cells.

Analysis of the MCV of the hematology control product of a high level of RBCs provides that the MCV of the product has a MCV value that changes less than 3 femtoliters (ftL) over a period of over 200 days. Comparison of a hematology control product with a high level of RBCs without the xanthine compound provides a MCV value that changes greater than 6 ftL over a period of 200 days. The suspension media of this invention renders the blood cell volume of the hematology control product less sensitive to longer storage times.

EXAMPLE 2

Hematology Control Product with a Red Blood Cell Component and White Blood Cell Component In a second embodiment, the suspension media is useful as a suspending media for components contained in a hematology control product used in the determination of red blood cell parameters and differentiation of white blood cells into three subpopulations. A comparison of the utility of the suspension media of this invention was made by using a suspension media of Table 1 containing caffeine and a suspension media of Table 1 without caffeine.

The red blood cell component is prepared according to the method as provided in Example 1. The white blood cell component is prepared in accordance with the disclosure in U.S. Pat. No. 4,704,364 to Carver, et al. with substitution of goose blood cells in place of turkey blood cells in preparation of the mononuclear cell analogs and substitution of alligator blood cells instead of shark blood cell in the preparation of the granulocyte analogs.

Four products are made from the red blood cell component and white blood cell component. Product 1 contains a low level of red blood cells, a quantity of the white blood cell component and the suspension media without caffeine. Product 2 contains the same low level of red blood cells as Product 1, the same quantity of the white blood cell component as Product 1 and the suspension media with caffeine. Product 3 contains a high level of red blood cells, a higher quantity of the white blood cell component than Product 1 and the suspension media without caffeine. Product 4 contains the same high level of red blood cells as Product 3, the same quantity of the white blood cell component as Product 3 and the suspension media with caffeine.

Bovine serum albumin (BSA) at a concentration of approximately 2% w/v is added to Products 1, 2, 3 and 4. The BSA acts as a protein source and improves the white blood cell component position in the resulting histogram.

Figure 1:
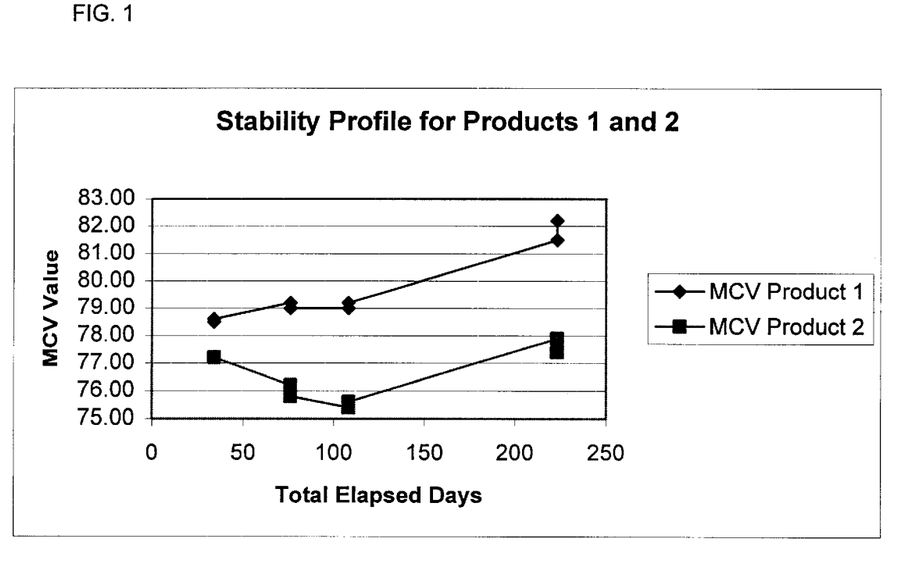
FIG. 1 graphically shows the change in MCV over total elapses days from production (TED) of Product 2 which contains a low level of red blood cells, a white blood cell component which simulates three populations of white blood cells and contains a xanthine compound compared to Product 1 which contains the same components but does not contain a xanthine compound.

Comparison of the change in MCV over total elapse days from production (TED) shows that Product 2 has a greater MCV stability than Product 1. This is shown in Table 2. Duplicate sample analysis at the indicated day was performed. More specifically, it has been found that Product 2 which contains the xanthine compound, caffeine, has a MCV that deviates less than 2 ftL after 223 elapsed days compared to Product 1 which does not contain a xanthine compound has a MCV that deviates greater approximately 4 ftL after 223 elapsed days. This also graphically shown in accompanying FIG. 1.

TABLE 2

Comparison of Product 1 and Product 2

| TED | MCV Product 1 | MCV Product 2 |
|---|---|---|
| 34 | 78.50 | 77.20 |
| 34 | 78.60 | 77.20 |
| 76 | 79.20 | 76.20 |
| 76 | 79.00 | 75.80 |
| 108 | 79.00 | 75.40 |
| 108 | 79.20 | 75.60 |
| 223 | 81.50 | 77.90 |
| 223 | 82.20 | 77.40 |

Figure 2:
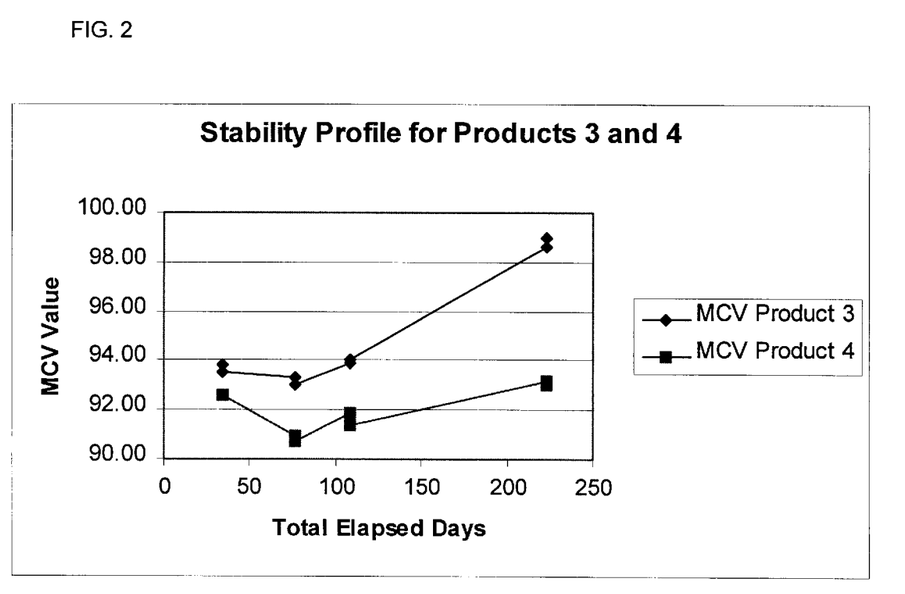
FIG. 2 graphically shows the change in MCV over TED of Product 4 which contains a high level of red blood cells, a white blood cell component which simulates three populations of white blood cells and contains a xanthine compound compared to Product 3 which contains the same components but does not contain a xanthine compound.

To further illustrate that the effect of the xanthine compound, Product 3 and Product 4 were compared. Product 4 contains the same quantity of caffeine as Product 2. Product 3 does not contain caffeine. Comparison of the change in MCV over total elapse days from production (TED) shows that Product 4 has a greater MCV stability than Product 3. This is shown in Table 3. More specifically, it has been found that Product 4 which contains the xanthine compound, caffeine, has a MCV that deviates approximately 2 ftL over a time period of 223 days compared to Product 1 which does not contain the xanthine compound has a MCV that deviates approximately 6 ftL over a period of time of 223 days. This is also shown in accompanying FIG. 2.

TABLE 3

Comparison of the MCV of Product 3 and Product 4

| TED | MCV Product 3 | MCV Product 4 |
|---|---|---|
| 34 | 93.80 | 92.60 |
| 34 | 93.50 | 92.60 |
| 76 | 93.30 | 90.90 |
| 76 | 93.00 | 90.70 |
| 108 | 93.90 | 91.90 |
| 108 | 94.00 | 91.40 |
| 223 | 98.60 | 93.20 |
| 223 | 99.00 | 93.00 |

Figure 5:
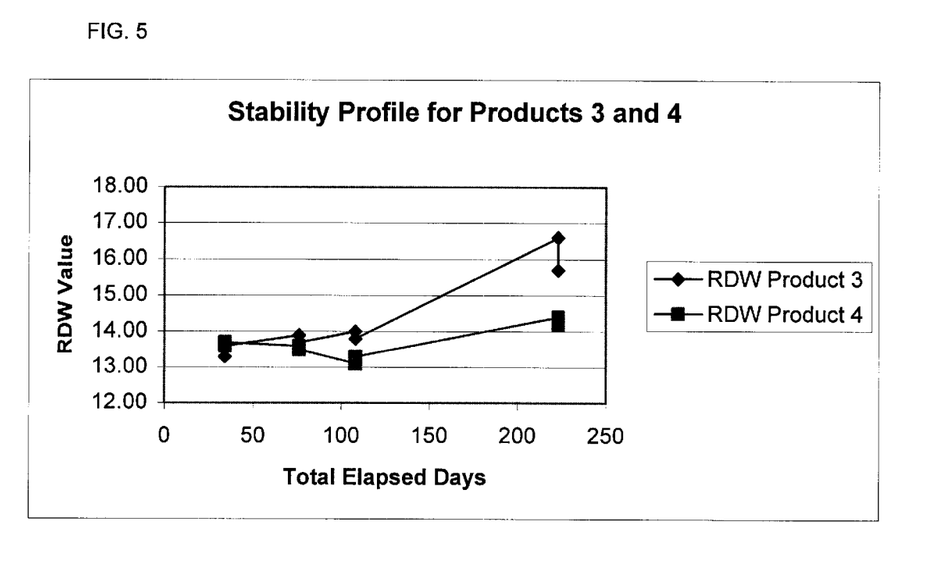
FIG. 5 graphically shows the change in RDW over TED of Product 4 compared to Product 3.

To further determine the utility of the suspension media, the RDW of Product 3 and Product 4 was compared. Comparison of the change in RDW over total elapse days from production (TED) shows that Product 4 has a greater RDW consistency from Product 3. This is shown in Table 4. Duplicate sample analysis at the indicated day was performed. More specifically, it has been found that Product 4 which contains the xanthine compound, caffeine, has a RDW that deviates less than 10% over the entire range of values during the 223 elapsed days compared to Product 3 which does not contain a xanthine compound has an RDW that deviates approximately 20% over the entire range of values during the 223 elapsed days. The deviation is also graphically shown in accompanying FIG. 5.

TABLE 4

Comparison of the RDW of Product 3 and Product 4

| TED | RDW Product 3 | RDW Product 4 |
|---|---|---|
| 34 | 13.30 | 13.60 |
| 34 | 13.60 | 13.70 |
| 76 | 13.90 | 13.60 |
| 76 | 13.70 | 13.50 |
| 108 | 14.00 | 13.10 |
| 108 | 13.80 | 13.30 |
| 223 | 16.60 | 14.40 |
| 223 | 15.70 | 14.20 |

EXAMPLE 3

Hematology Control Product with a Red Blood Cell Component and White Blood Cell Component In a third embodiment, the suspension media is useful as a suspending media for components contained in a hematology control product used in the determination of red blood cell parameters and differentiation of white blood cells into greater than four subpopulations. A comparison of the utility of the suspension media of this invention was made by using a suspension media of Table 1 containing caffeine and a suspension media of Table 1 without caffeine.

The red blood cell component is prepared according to the method as provided in Example 1. The red blood cell component is prepared according to the method as provided in Example 1. The white blood cell component is prepared in accordance with the disclosure in U.S. Pat. No. 5,529,933 to Young et al.

Four products are made from the red blood cell component and white blood cell component. Product 5 contains a low level of red blood cells, a quantity of the white blood cell and the suspension media without caffeine. Product 6 contains the same low level of red blood cells as Product 5, the same quantity of the white blood cell as Product 5 and the suspension media with caffeine. Product 7 contains a high level of red blood cells, a higher quantity of the white blood cell than Product 5 and the suspension media without caffeine. Product 8 contains the same high level of red blood cells as Product 7, the same quantity of the white blood cell as Product 7 and the suspension media with caffeine.

When a red blood cell component and white blood cell component are added to the suspension media for the determination of four or more white blood cell subpopulations are combined to provide a single multiple analysis reference blood cell control product for instruments which use lytic reagents, it is preferred that the suspension media contain an aqueous solution of bound cholesterol. The bound cholesterol improves the white blood cell component position in the resulting scatterplot. A suitable example of the most preferred bound cholesterol is Moducyte™, as described in U.S. Pat. No. 4,290,774, assigned to Miles, Inc., which is a high density lipoprotein cholesterol bound with albumen. The final concentration of cholesterol in the suspension media ranges from 100 to 1000 milligrams per liter, and preferably 200 to 700 milligrams per liter depending upon the cell count in the hematology control product. An alternate suitable commercial lipoprotein is SUPERTRATE (available from Bayer). It consists essentially of high-density lipoprotein (i.e., HDL) and is used at about 200 to 1200 milligrams per liter, and more preferably at about 300 to 800 grams per liter in the hematology control product. An antioxidant, such as a-Tocopherol, can be further added to the lipoprotein source to reduce peroxides produced by the oxidation of the lipoproteins. In the instant example, Moducyte at a concentration of approximately 2% w/v is used in Products 5, 6, 7 and 8 to improve the white blood cell position in the resulting histogram.

Figure 3:
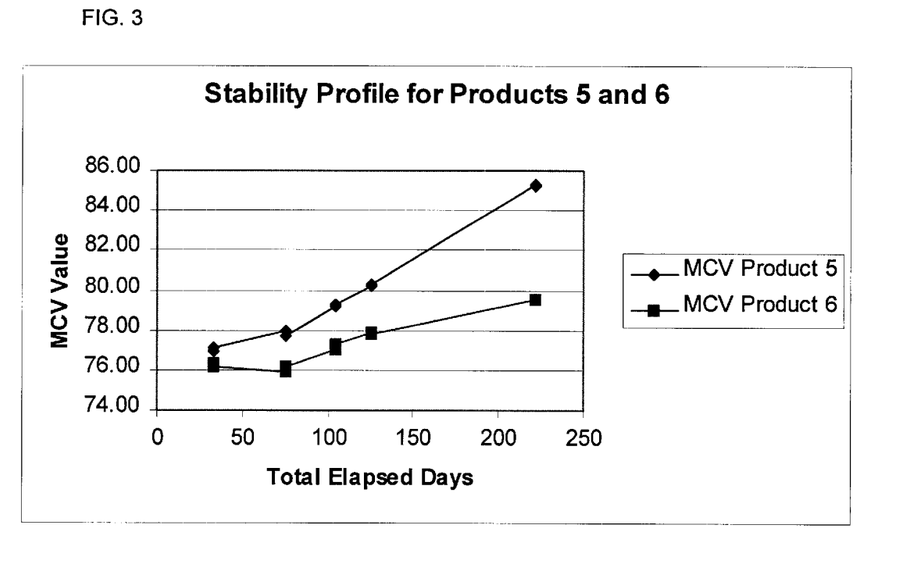
FIG. 3 graphically shows the change in MCV over TED of Product 6 which contains a low level of red blood cells, a white blood cell component which simulates four subpopulations of white blood cells and contains a xanthine compound compared to Product 5 which contains the same components but does not contain a xanthine compound.

Comparison of the change in MCV over total elapse days from production (TED) shows that Product 6 has a greater MCV stability than Product 5. This is shown in Table 5. More specifically, it has been found that Product 6 which contains the xanthine compound, caffeine, has a MCV that deviates less than approximately 4 ftL after 223 days compared to Product 5 which does not contain the xanthine compound, caffeine, has a MCV that deviates greater than 8 ftL after 223 days. This is also shown in accompanying FIG. 3.

TABLE 5

Comparison of the MCV of Product 5 and Product 6

| TED | MCV Product 5 | MCV Product 6 |
|---|---|---|
| 33 | 76.90 | 76.30 |
| 33 | 77.10 | 76.20 |
| 75 | 78.00 | 75.90 |
| 75 | 77.70 | 76.20 |
| 104 | 79.20 | 77.00 |
| 104 | 79.30 | 77.30 |
| 126 | 80.20 | 77.90 |
| 126 | 80.30 | 77.80 |
| 222 | 85.30 | 79.50 |
| 222 | 85.20 | 79.50 |

Figure 4:
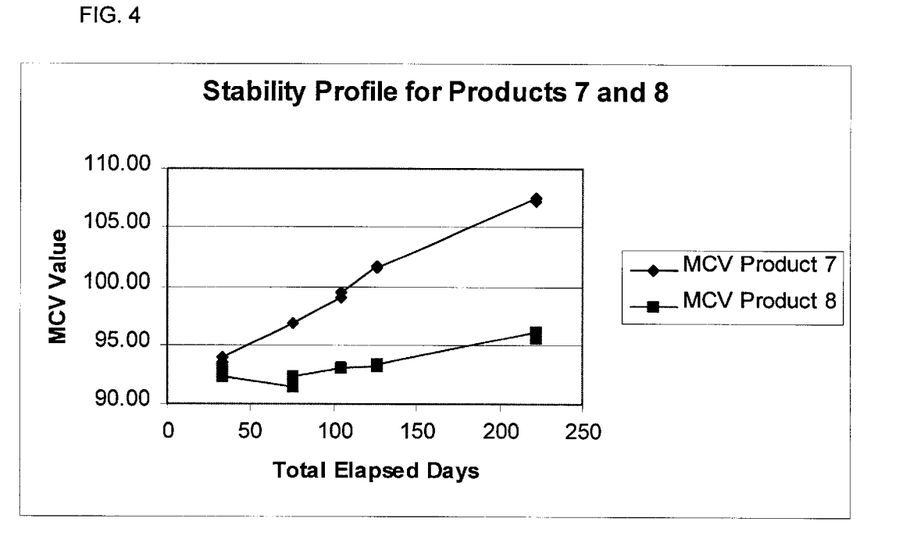
FIG. 4 graphically shows the change in MCV over TED of Product 8 which contains a high level of red blood cells, a high level of white blood cell component which simulates four subpopulations of white blood cells and contains a xanthine compound compared to Product 7 which contains the same components but does not contain a xanthine compound.

To further illustrate that the effect of the xanthine compound, Product 7 and Product 8 were compared. Product 8 contains the same quantity of caffeine as Product 6. Comparison of the change in MCV over total elapse days from production (TED) shows that Product 8 has a greater MCV stability than Product 7. This is shown in Table 6. More specifically, it has been found that Product 8 which contains the xanthine compound, caffeine, has a MCV that deviates less than 5 ftL after 223 days compared to Product 5 which does not contain the xanthine compound, caffeine, has a MCV that deviates approximately 11 ftL after 223 days. This is also shown in accompanying FIG. 4.

TABLE 6

Comparison of the MCV of Product 7 and Product 8

| TED | MCV Product 7 | MCV Product 8 |
| --- | --- | --- |
| 33 | 93.50 | 93.00 |
| 33 | 94.00 | 92.40 |
| 75 | 96.90 | 91.50 |
| 75 | 96.90 | 92.30 |
| 104 | 99.00 | 93.00 |
| 104 | 99.50 | 93.00 |
| 126 | 101.70 | 93.20 |
| 126 | 101.60 | 93.40 |
| 222 | 107.50 | 96.20 |
| 222 | 107.20 | 95.50 |

Figure 6:
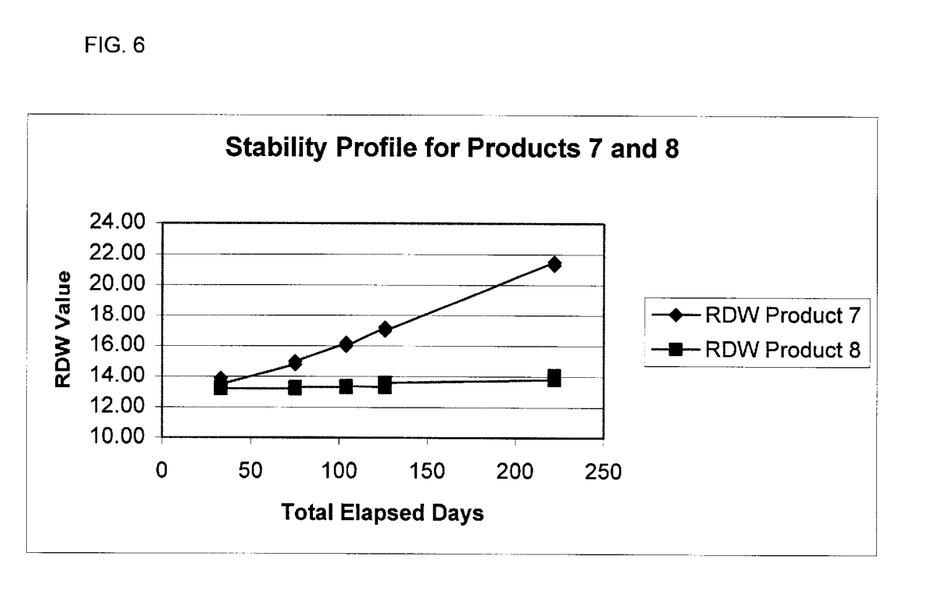
FIG. 6 graphically shows the change in RDW over TED of Product 8 compared to Product 7.

To further determine the utility of the suspension media, the RDW of Product 7 and Product 8 was compared. Comparison of the change in RDW over total elapse days from production (TED) shows that Product 8 has a greater RDW consistency than Product 7. This is shown in Table 7. Duplicate sample analysis at the indicated day was performed. More specifically, it has been found that Product 8 which contains the xanthine compound, caffeine, has a RDW that deviates less than 5% over the entire range of values during the 223 elapsed days compared to Product 7 which does not contain a xanthine compound has an RDW that deviates greater than 10% over the entire range of values during the 223 elapsed days. The deviation is also graphically shown in accompanying FIG. 6.

TABLE 7

Comparison of RDW of Product 7 and Product 8

| TED | RDW Product 7 | RDW Product 8 |
| --- | --- | --- |
| 33 | 13.90 | 13.30 |
| 33 | 13.50 | 13.20 |
| 75 | 14.80 | 13.20 |
| 75 | 15.00 | 13.30 |
| 104 | 16.20 | 13.30 |
| 104 | 16.00 | 13.40 |
| 126 | 17.20 | 13.30 |
| 126 | 17.00 | 13.60 |
| 222 | 21.50 | 13.80 |
| 222 | 21.30 | 14.10 |

EXAMPLE 4

Hematology Control Product with Inventive Suspension Media Compared with Commercial Products A comparison of the utility of the suspension media of this invention was made by using a suspension media of Table 1 containing caffeine used in a hematology control product containing a red blood cell component and a white blood cell component compared to a commercially produced hematology control product using a suspension media without caffeine containing the same quantity of the red blood cell component and the same quantity of the white blood cell component. Product 9 was the same as Product 2 described above in Example 2. Product 10 was the same as Product 1 described above in Example 2, except that the suspension media was prepared according to U.S. Pat. No. 4,358,394 to Crews et al (1982). Product 11 was the same as Product 6 described above in Example 3. Product 12 was the same as Product 5 described above in Example 3, except that the suspension media was prepared according to U.S. Pat. No. 5,529,933 to Young et al (1996).

It has been found that the amount of change in MCV in Product 9 is significantly less than the amount of change in MCV of Product 10, In addition, it has been found that the amount of change in MCV in Product 11 is significantly less than the amount of change in MCV of Product 12. Moreover, the equilibration period of time for Products 9 and 11 are uniform and not dependent on MCV level nor RBC concentration, and thus simplifies manufacturing logistics.

In the present specification a detailed description of the invention has been set forth for the purpose of illustration. It will be appreciated, however, that various changes can be made without departing from the spirit of the invention, and such changes are intended to fall within the scope of the appended claims.

We claim:

1. A hematology control product comprising a closed vial of a lyseable red blood cell component and a xanthine compound in an isotonic suspension medium, wherein said xanthine compound is in an amount sufficient to provide a shelf life of greater than 60 days of the hematology control product and wherein said lyseable red blood cell component is present in an amount sufficient to be measurable with an automated hematology instrument and wherein said hematology control product has an reported mean cell volume which corresponds substantially with the mean cell volume of human whole blood.

2. The hematology control product of claim 1, wherein the hematology control product has an osmolality from about 200 to 400 milliosmoles.

3. The hematology control product of claim 2, which further comprises compatible preservative compositions in an amount sufficient to provide fungicidal and bactericidal activity.

4. The hematology control product of claim 3, which contains potassium, sodium chloride, phosphate and sulfate ions each in the amount from approximately 0.001 to 0.1 moles.

5. The hematology control product of claim 2, where the xanthine compound is from about 0.1 to 1.0% by weight/volume.

6. The hematology control product of claim 2, where the xanthine compound is present in an amount of from about 0.2 to 0.7% by weight/volume.

7. The hematology control product of claim 1, which further comprises a white blood cell component.

8. The hematology control product of claim 7, wherein the white blood cell component simulates at least three subpopulations of white blood cells.

9. The hematology control product of claim 8, wherein the white blood cell component simulates five subpopulations of white blood cells.

10. A hematology control product comprising a closed vial of a lyseable red blood cell component and caffeine in an isotonic suspension medium, wherein said caffeine is in an amount sufficient to provide a shelf life of greater than 60 days of the hematology control product and wherein said lyseable red blood cell component is present in an amount sufficient to be measurable with an automated hematology instrument and wherein said hematology control product has an reported mean cell volume which corresponds substantially with the mean cell volume of human whole blood.

11. The hematology control product of claim 10, which further comprises one or more pH adjusting agents to provide a pH in the range from approximately 5.8 to 6.8.

12. A method of using a hematology control product to determine the accuracy and reproducibility of the operation of a hematology instrument comprising the steps of:
 a) providing the hematology control product comprising a lyseable red blood cell component and a xanthine compound in an isotonic suspension medium, wherein said xanthine compound is in an amount sufficient to provide a shelf life of greater than 60 days of the hematology control product and wherein said lyseable red blood cell component is present in an amount sufficient to be measurable with an automated hematology instrument and wherein said hematology control product has an reported mean cell volume which corresponds substantially with the mean cell volume of human whole blood, and wherein said hematology control product has a known reference value for each component type present in the product;
 b) determining the reference value for each component type in the hematology control product with an automated hematology instrument; and
 c) comparing the reference value for each component type obtained from step b) above with the known reference value for each component type from step a) above.

13. The method of claim 12, wherein the reference value comprises a mean cell volume value.

14. The method of claim 13, wherein the reference value further comprises a red blood cell distribution width value.

15. The method of claim 12, wherein the hematology control product has an osmolality from about 200 to 400 milliosmoles.

16. The method of claim 12, wherein the xanthine compound is from about 0.1 to 1.0% by weight/volume.

17. The method of claim 16, wherein the hematology control product further comprises a white blood cell component.

18. The method of claim 17, wherein the white blood cell component simulates at least three subpopulations of white blood cells.

19. The method of claim 17, wherein the white blood cell component simulates five subpopulations of white blood cells.

20. The method of claim 12, wherein the xanthine compound is present in an amount of from about 0.2 to 0.7% by weight/volume.

21. A method of using a hematology control product to determine the accuracy and reproducibility of the operation of a hematology instrument comprising the steps of:
 a) providing said hematology control product comprising a lyseable red blood cell component and caffeine in an isotonic suspension medium, wherein said caffeine is in an amount sufficient to provide a shelf life of greater than 60 days of said hematology control product and wherein said lyseable red blood cell component is present in an amount sufficient to be measurable with an automated hematology instrument and wherein said hematology control product has an reported mean cell volume which corresponds substantially with the mean cell volume of human whole blood, and wherein said hematology control product has a known reference value for each component type present in the product;
 b) determining the reference value for each component type in the hematology control product with an automated hematology instrument; and
 c) comparing the reference value for each component type obtained from step b) above with the known reference value for each component type from step a) above.

22. The method of claim 21, wherein the hematology control product further comprises one or more pH adjusting agents to provide a pH in the range from approximately 5.8 to 6.8.

* * * * *